United States Patent [19]

Wee

[11] Patent Number: 4,891,058
[45] Date of Patent: Jan. 2, 1990

[54] 1-ALKYL-3-ARYL IMIDAZOLIDINE-2,4-DIONES AND HERBICIDAL USE

[75] Inventor: Siok H. H. Wee, Berkeley, Calif.

[73] Assignee: ICI Americas Inc., Wilmington, Del.

[21] Appl. No.: 220,299

[22] Filed: Jul. 18, 1988

[51] Int. Cl.$^4$ ............... A01N 37/18; C07C 103/28
[52] U.S. Cl. ...................... 71/118; 564/164; 564/165; 564/194
[58] Field of Search .............. 564/164, 165, 194; 71/118

[56] References Cited

U.S. PATENT DOCUMENTS

| | | | |
|---|---|---|---|
| 2,794,835 | 6/1957 | Löfgran et al. | 564/194 |
| 3,812,147 | 5/1974 | Adams et al. | 564/194 X |
| 3,888,899 | 6/1975 | Greve et al. | 558/393 |
| 3,928,415 | 12/1975 | Greve et al. | 560/9 |
| 4,237,068 | 12/1980 | Boyes et al. | 564/194 |
| 4,473,694 | 9/1984 | Lai | 564/194 X |
| 4,532,251 | 7/1985 | Spatz | 514/354 |
| 4,596,813 | 6/1986 | Spatz | 514/355 |
| 4,623,383 | 11/1986 | Grega et al. | 71/100 |
| 4,639,468 | 1/1987 | Roncucci et al. | 564/194 X |

FOREIGN PATENT DOCUMENTS 220329 2/1957 Australia.
839943 6/1960 United Kingdom.

OTHER PUBLICATIONS

Mel'nikov et al., Chemical Abstracts, vol. 70 (1969) 87173a.
Telc et al., Chemical Abstracts, vol. 76 (1972) 152718x.
Akerman et al., Chemical Abstracts, vol. 79 (1973) 104t.
Mulliez et al., Chemical Abstracts, vol. 95 (1981) 204400b.
Joa Eujo, Chemical Abstracts, vol. 101 (1984) 7177a.
Bajusz et al., Chemical Abstracts, vol. 103 (1985) 70951e.
Roloff et al., Chemical Abstracts, vol. 105 (1986) 133,746f.
Slouka et al., Chemical Abstracts, vol. 105 (1986) 226068b.
Saito et al., Chemical Abstracts, vol. 107 (1987) 77727c.
Pantsurkin et al., Chemical Abstracts, vol. 108 (1988) 55404p.

*Primary Examiner*—Richard L. Raymond
*Attorney, Agent, or Firm*—Harry A. Pacini; Denis A. Polyn

[57] ABSTRACT

1-alkyl-3-arylimidazolidine-2,4-diones are prepared by reacting the herbicidally active intermediate N-phenyl-2-substituted-2-alkylamino acetamides with 1,1'-carbonyldiimidazole in a suitable solvent. These herbicidally active intermediates are prepared by reacting alpha-haloacetanilides with the primary amine of choice in an alcohol solvent, in the presence or absence of water, at ambient temperature.

32 Claims, No Drawings

1-ALKYL-3-ARYL IMIDAZOLIDINE-2,4-DIONES AND HERBICIDAL USE

Certain imidazolidine-2,4-diones are useful as herbicides. Intermediates for these compounds have been produced by various methods, including reaction of an N-aryl-2,2,2-trihaloacetanilide with an N-alkyl-2-haloacetamide, an inorganic base and catalyst or a metal hydride base as described in the accompanying patent application of Siok Hui Helena Wee et al., entitled "NOVEL 5-SUBSTITUTED-2,4-IMIDAZOLIDINEDIONES", commonly assigned (U.S. Ser. No. 07/220,298, filed July 17, 1988) and concurrently filed herewith.

Certain N-phenyl-2-substituted-2-alkylamino acetamides have been found to be useful as fungicides (U.S. Pat. Nos. 4,532,251 and 4,596,813, issued to David M. Spatz), while still others have been found useful as pharmaceuticals (U.S. Pat. Nos. 3,888,899 and 3,928,415, issued to Heinz Gunter Greve et al.).

SUMMARY OF THE INVENTION

The intermediate N-phenyl-2-substituted-2-alkylamino acetamides of this invention have been found to be useful as herbicides. Such compounds have been produced by refluxing the alpha-haloacetanilide with the primary amine of choice, either in a hydrocarbon solvent or using an excess of the primary amine (U.S. Pat. Nos. 4,532,251, 4,596,813, 3,888,899 and 3,928,415, above) as shown by the following scheme I:

Scheme I

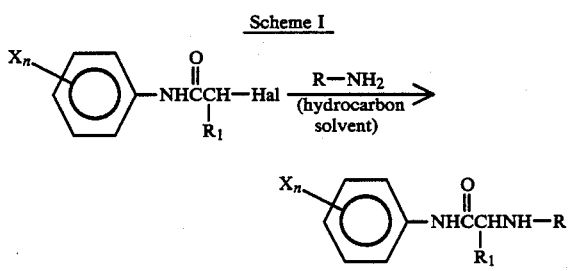

wherein R is lower alkyl; $R_1$ is hydrogen, $C_1$–$C_3$ lower alkyl, phenyl, phenyl substituted with phenoxy, benzyloxy or nitro or phenyl substituted with alkyl, $C_1$–$C_3$ lower alkoxy, haloalkyl, halo or combinations thereof; and X is $C_1$–$C_3$ alkyl, halo, haloalkyl or combinations thereof, and n is an integer from 0–3, inclusive.

It has been found that the herbicidally active acetamide intermediates of the present invention can be produced by reacting the alpha-haloacetanilide with the primary amine of choice in an alcohol solvent, in the presence or absence of water, at ambient temperature as shown by the following Scheme II:

Scheme II

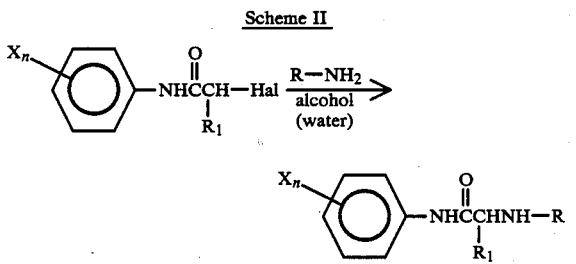

wherein R, $R_1$ X and n are as defined above.

One process of this invention embodies herbicidally active compounds having the formula

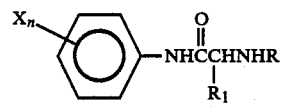

wherein R, $R_1$, X and n are as defined above.

The preferred amine of this reaction is a lower alkyl primary amine, preferably methyl or ethyl. The preferred base of this reaction is an excess of the intermediate amine. The preferred solvents of this reaction are alcohol, water of alcohol and water, preferably alcohol. The preferred temperature of this reaction is ambient.

This reaction can be run at atmospheric or superatmospheric pressure, preferably at atmospheric pressure.

Another process of this invention embodies compounds having the formula

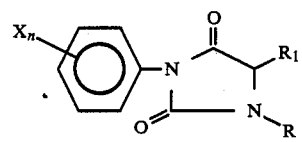

wherein R, $R_1$, X and n are as defined above.

In a process of this invention, the intermediate acetamide is reacted with 1,1'-carbonyldiimidazole in a suitable solvent as shown by the following Scheme III

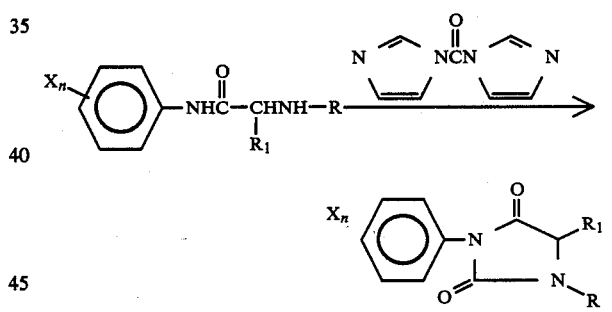

wherein R, $R_1$, X and n are as defined above. The resulting products are herbicidal in their own right and can be further reacted at the 5-position to produce still other herbicidally active products.

The preferred acetamides of this invention are those substituted with lower alkyl. The preferred solvents of this reaction are hydrocarbons and chlorinated hydrocarbons, preferably dichloroethane or benzene, more preferably benzene.

The preferred temperatures of this reaction are from about 40 to about 120° C., preferably from about 60° to about 100° C., most preferably 80° C. The reaction can be run at subatmospheric, atmospheric or superatmospheric pressure, preferably atmospheric pressure.

The term "lower alkyl" includes both straight and branched chain saturated acyclic hydrocarbyl moieties and includes such moieties having from 1 to 3 carbon atoms such as methyl, ethyl, n-propyl and isopropyl. The term "halo" includes fluorine, chlorine, bromine or iodine as mono-, di-, tri- and mixed halogen substitutions.

The compounds of this invention have been found to be active herbicides in possessing herbicidal activity against various species of weeds. In the broadest sense, the term "weeds" refers to plants which grow in locations in which they are not desired.

This invention also therefore relates to a method for controlling undesirable vegetation, comprising applying to a locus where control of such vegetation is desired an herbicidally effective amount of a compound as described herein, and also relates to herbicidal compositions of matter comprising an herbicidally effective amount of a compound as described herein, together with an inert diluent or carrier suitable for use with herbicides.

As used herein the term "herbicide" refers to compounds which adversely control or modify the growth of plants, particularly of undesirable plants. By the term "herbicidally effective amount" is meant an amount of compound which causes an adverse controlling or modifying effect on the growth of plants. The term "plants" is meant to include germinant seeds, emerging seedlings, and established vegetation, including roots and above-ground portions. Such adverse modifying and controlling effects may include all deviations from natural development.

The following are examples of the preparation of compounds and processes of this invention, the structures of which were confirmed by infrared, nuclear magnetic resonance and mass spectroscopy.

EXAMPLE 1

Preparation of N-(2-Fluoro)phenyl sarcosine amide
N-(2-Fluoro)phenyl sarcosine amide To an ethanolic (70 ml) solution of N-(2-fluoro)phenyl-2-chloroacetamide (21.6 g, 0.11 mol) was added 40% aqueous methylamine (70 ml) and stirred at room temperature overnight. The mixture was concentrated on a rotary evaporator. The product was extracted into ethyl ether (200 ml) and the organic layer dried with magnesium sulfate and concentrated. The crude product was passed through a short column of silica gel using 1:1 methylene chloride-hexane as the eluent. The product obtained was a yellow oil weighing 18.2 g (88% yield).

EXAMPLE 2

Preparation of N-(3-trifluoromethyl)phenyl sarcosine amide

To an ethanolic solution (50 ml) of N-(3-trifluoromethyl)phenyl-2-bromoacetamide (2.8 g, 0.01 mol) cooled in an ice/water bath was added subsurface methylamine until saturation was reached. The mixture was stirred overnight at ambient temperature, then concentrated by rotary evaporator. The product was extracted into dichloromethane, washed with water and the organic layer dried with magnesium sulfate and evaporated to dryness by rotary evaporator to yield 2.2 g (95% yield) of an oil.

EXAMPLE 3

Preparation of 3-(2-Fluoro)phenyl-2,4-dioxo-1-methylimidazolidine

To a benzene (25 ml) solution of N-(2-fluoro)phenyl sarcosine amide (2.0 g, 10 mmol) was added 1,1'-carbonyldiimidazole (2.0 g, 12 mmol). The mixture was heated under reflux overnight, diluted with ethyl acetate (25 ml) and washed with water (40 ml). The organic layer was dried with magnesium sulfate and concentrated on a rotary evaporator to give 2.2 g (96% yield) of product.

The following Table 1 illustrates embodiments of this invention. Structures of the indicated compounds were confirmed by spectral analysis.

TABLE 1

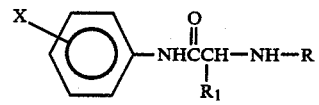

| Compound Number | X | R | $R_1$ | $n_D^{30}$ or m.p. °C. |
|---|---|---|---|---|
| 1 | 2-F | —CH$_3$ | H | thick oil |
| 2 | 2,5-di-F | —CH$_3$ | H | 60–65 |
| 3 | 2,5-di-F | —CH$_3$ | —C$_6$H$_5$ | 95–100 |
| 4 | 3-CF$_3$ | —CH$_2$CH$_3$ | —C$_6$H$_5$ | thick oil |
| 5 | 2,5-di-F | —CH$_2$CH$_3$ | H | thick oil |
| 6 | 2,5-di-F | —CH$_3$ | —C$_2$H$_5$ | thick oil |
| 7 | 2,5-di-F | —CH$_3$ | —CH$_3$ | 50–53 |
| 8 | 2,5-di-F | —CH$_3$ | —C$_6$H$_4$Cl | 68–71 |

TABLE 1-continued structure: X-C6H4-NHC(O)CH(R1)-NH-R

| Compound Number | X | R | R₁ | $n_D^{30}$ or m.p. °C. |
|---|---|---|---|---|
| 9 | 2,5-di-F | —CH₃ | 3-CF₃-phenyl | 70–73 |
| 10 | 3,4-di-Cl | —CH₃ | phenyl | 105–107 |
| 11 | 3-CF₃ | —CH₃ | H | oil |
| 12 | 2,5-di-F | —CH₃ | 3,4-di-Cl-phenyl | 92–95 |
| 13 | 2,5-di-F | —CH₃ | 4-CH₃-phenyl | thick oil |
| 14 | 3-CF₃ | —CH₃ | 3-Cl-phenyl | thick oil |
| 15 | 3-CF₃ | —CH₃ | 4-Br-phenyl | thick oil |
| 16 | 2,5-di-F | —CH₃ | 4-Br-phenyl | thick oil |
| 17 | 3-Cl | —CH₂CH₃ | phenyl | thick oil |
| 18 | 3-CF₃ | —CH₂CH₃ | 3-Cl-phenyl | thick oil |
| 19 | 3-CF₃ | —CH₂CH₃ | 3-Br-phenyl | 75–77 |

TABLE 1-continued
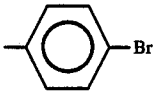
| Compound Number | X | R | R₁ | $n_D^{30}$ or m.p. °C. |
|---|---|---|---|---|
| 20 | 2,4-di-F | —CH₂—CH₃ | 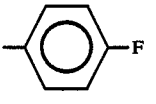 4-Br-phenyl | 65–70 |
| 21 | 3-CF₃ | —CH₂CH₃ | 4-F-phenyl | thick oil |
| 22 | 2-Cl | —CH₃ | phenyl | liquid |
| 23 | 3-CF₃ | —CH₂CH₃ | 3-CF₃-phenyl | thick oil |
| 24 | 3-CF₃ | —CH₂CH₃ | 2-F-phenyl | oil |
| 25 | 2-F | —CH₂CH₃ | 3-CF₃-phenyl | oil |
| 26 | 2,5-di-F | —CH₃ | 2,5-di-Cl-phenyl | oil |
| 27 | 2-F—5-CF₃ | —CH₂CH₃ | phenyl | oil |
| 28 | 2,5-di-F | —CH₃ | 4-C(CH₃)₃-phenyl | oil |
| 29 | 2,5-di-F | —CH₃ | 4-I-phenyl | oil |

TABLE 1-continued structure: X-phenyl-NHC(=O)CH(R1)-NH-R

| Compound Number | X | R | R1 | $n_D^{30}$ or m.p. °C. |
|---|---|---|---|---|
| 30 | 2,5-di-F | —CH₃ | 4-phenoxyphenyl | oil |
| 31 | 2,5-di-F | —CH₃ | 4-F-phenyl | oil |
| 32 | 2,5-di-F—4-CH₃ | —CH₃ | 4-Cl-phenyl | 96–99 |
| 33 | 2,5-di-F | —CH₃ | 3-Br-phenyl | oil |
| 34 | 2,5-di-F | —CH₃ | 3-Cl-phenyl | oil |
| 35 | 2,5-di-F | —CH₃ | 3-OCH₃-phenyl | oil |
| 36 | -3-CF₃ | —CH₂CH₃ | 2,4-di-F-phenyl | 60–65 |
| 37 | 3-CF₃ | —CH₂CH₃ | 3-Br-phenyl | oil |
| 38 | 2,5-di-F | —CH₃ | 4-(OCH₂-phenyl)-phenyl | 117–125 |
| 39 | 3-CF₃ | —CH₃ | 2-F-phenyl | oil |

TABLE 1-continued $$\underset{R_1}{\underset{|}{X-\text{C}_6\text{H}_4-\text{NHC}(\text{O})\text{CH}-\text{NH}-\text{R}}}$$

| Compound Number | X | R | $R_1$ | $n_D^{30}$ or m.p. °C |
|---|---|---|---|---|
| 40 | 3-CF$_3$ | —CH$_2$CH$_3$ | (phenyl with NO$_2$) | oil |
| 41 | 3-CF$_3$ | —CH$_2$CH$_3$ | (phenyl with Cl) | 87–90 |
| 42 | 3-CF$_3$ | —CH$_2$CH$_3$ | (phenyl with F, F) | oil |

The compounds listed in the foregoing Table 1 were tested for herbicidal activity by various methods and at various rates of application. Some were tested by more than one method or at more than one rate, but at least one method is shown for each compound to exhibit utility. The following examples are for illustrative purposes only and are not intended as necessariliy representative of the overall testing performed. As one skilled in the art is aware, in herbicidal testing a significant number of factors that are not readily controllable can affect the results of individual tests. For example, the results may vary depending on environmental factors, such as amount of sunlight and water, soil type, pH of the soil, temperature, and humidity, among other factors. Also, the depth of planting and the application rate of the herbicide, as well as the nature of crops being tested, can affect the results of the test. Results may vary from crop to crop and within the crop varieties. The methods and activity are as follows:

Pre-Emergence Herbicidal Evaluation

Flats were filled with sandy loam soil containing a fungicide and fertilizer. The soil was leveled and rows of grassy weeds, broadleaf weeds and yellow nutsedge (*Cyperus esculentus*), were planted thickly enough so that several seedlings emerged per inch of row. The grassy weeds were: foxtail (Setaria spp.), watergrass (*Echinochloa crusgalli*) and wild oat (*Avena fatua*). Broadleaf weeds utilized were annual morningglory (*Ipomoea purpurea*), velvetleaf (*Abutilon theophrasti*) and mustard (*Brassica kaber*).

One day after planting, the flats were sprayed with a solution of a test compound at a rate of 80 gallons of solution per acre with the compound being applied at a rate of 4 pounds per acre (4.48 kg/ha).

The solutions of the test compounds were made by weighing out 333 mg of the test compound into a 60 ml wide-mouth bottle, dissolving it in 25 ml of acetone containing 1% Tween ®20 (polyoxyethylene sorbitan monolaurate emulsifier). Additional solvents, not exceeding 5 ml, were used if needed to dissolve the compound. A 20.5 ml aliquot was taken from the stock solution and diluted with 25 ml of an acetone:water mixture (19:1) containing 1% Tween ®20. This was used as the spray solution.

The flats were returned to the greenhouse after spraying and watered daily by sprinkling. The degree of weed control was estimated and recorded 18 days after treatment, as percentage control compared to the growth of the same species in an untreated check flat of the same age.

The percent control is based on the total injury to the plants due to all factors, including inhibited germination, killing of the plant tissue after emergence, stunting, malformation, chlorosis, and other types of injury. The control ratings vary from 0 to 100 percent, where 0 represents no effect with growth equal to the untreated control, and 100 represents complete kill.

POST-EMERGENCE HERBICIDAL EVALUATION

The soil was prepared and seeded with the same varieties as described for the pre-emergence test. The flats were placed in the greenhouse at 70°–85° F. and watered by sprinkling. Twelve to fourteen days after planting, the flats were sprays at a rate of 80 gallons of solution per acre. The compound was applied at the rate of 4 pounds/ acre (4.48 kg/ha). The spray solution was made up similarly to that described for the pre-emergence evaluation.

The flats were returned to the greenhouse after spraying and watered daily without wetting the foliage. Eighteen days after treatment the degree of weed control was estimated and recorded as percentage control compared to the growth of the same species in an untreated check flat of the same age. The percent control ratings were assigned on the same basis as for the pre-emergence evaluation.

The following Table II contains the results of these tests, in terms of average control of the three grasses, three broadleaf weeds, and yellow nutsedge, respectively, in both pre- and post-emergence evaluations.

| KEY TO TABLE 2 | | |
|---|---|---|
| green foxtail | *Setaria viridis* | SETVI |
| watergrass | *Echinochloa crusgalli* | ECHOG |
| wild oat | *Avena fatua* | AVEFA |
| annual morningglory | *Ipomoea purpurea* | PHBPU |

-continued

| KEY TO TABLE 2 | | |
|---|---|---|
| velvetleaf | *Abutilon theophrasti* | ABUTH |
| wild mustard | *Brassica kaber* | SINAR |
| yellow nutsedge | *Cyperus esculentus* | CYPES |
| AVG | Average grasses | |
| AVB | Average broadleaf | |

TABLE 2

Rating at 4 lb/A

| Compound No. | METHOD | SETVI | ECHCG AVEFA | PHBPU | ABUTH | SINAR | CYPES | AVG | AVB |
|---|---|---|---|---|---|---|---|---|---|
| 1 | PRE | 0 | 80 | 10 | 10 | 80 | 95 | 0 | 30 | 62 |
|   | POS | 0 | 0 | 0 | 0 | 5 | 0 | 0 | 0 | 2 |
| 2 | PRE | 10 | 95 | 10 | 100 | 100 | 95 | 0 | 38 | 98 |
|   | POS | 0 | 0 | 0 | 10 | 0 | 0 | 0 | 0 | 3 |
| 3 | PES | 85 | 60 | 0 | 100 | 80 | 100 | 0 | 48 | 93 |
|   | POS | 0 | 0 | 0 | 0 | 0 | 10 | 0 | 0 | 3 |
| 4 | PES | 90 | 0 | 0 | 0 | 0 | 20 | 0 | 30 | 7 |
|   | POS | 0 | 10 | 0 | 10 | 10 | 10 | 0 | 3 | 10 |
| 5 | PRE | 80 | 0 | 0 | 0 | 0 | 50 | 0 | 27 | 17 |
|   | POS | 0 | 0 | 0 | 0 | 0 | 0 | 0 | 0 | 0 |
| 6 | PES | 80 | 0 | 0 | 0 | 0 | 0 | 0 | 27 | 0 |
|   | POS | 0 | 0 | 0 | 0 | 0 | 0 | 0 | 0 | 0 |
| 7 | PES | 80 | 0 | 0 | 0 | 80 | 90 | 0 | 27 | 57 |
|   | POS | 0 | 0 | 0 | 0 | 0 | 0 | 0 | 0 | 0 |
| 8 | PES | 100 | 100 | 90 | 100 | 100 | 100 | 0 | 97 | 100 |
|   | POS | 0 | 0 | 0 | 10 | 0 | 0 | 0 | 0 | 3 |
| 9 | PES | 100 | 90 | 100 | 100 | 100 | 100 | 0 | 97 | 100 |
|   | POS | 0 | 0 | 0 | 0 | 0 | 10 | 0 | 0 | 3 |
| 10 | PES | 100 | 40 | 0 | 20 | 100 | 100 | 30 | 47 | 73 |
|   | POS | 0 | 0 | 0 | 40 | 100 | 100 | 0 | 0 | 80 |
| 11 | PRE | 90 | 30 | 30 | 85 | 90 | 100 | 0 | 50 | 92 |
|   | POS | 0 | 0 | 0 | 0 | 0 | 90 | 0 | 0 | 30 |
| 12 | PES | 100 | 100 | 100 | 100 | 100 | 100 | 0 | 100 | 100 |
|   | POS | 0 | 0 | 0 | 0 | 30 | 100 | 0 | 0 | 43 |
| 13 | PES | 90 | 90 | 20 | 50 | 100 | 100 | 0 | 67 | 83 |
|   | POS | 0 | 0 | 0 | 0 | 0 | 0 | 0 | 0 | 0 |
| 14 | PES | 90 | 0 | 0 | 0 | 0 | 0 | 0 | 30 | 0 |
|   | POS | 0 | 0 | 0 | 0 | 0 | 0 | 0 | 0 | 0 |
| 15 | PES | 50 | 0 | 0 | 0 | 0 | 0 | 0 | 17 | 0 |
|   | POS | 0 | 0 | 0 | 0 | 0 | 0 | 0 | 0 | 0 |
| 16 | PES | 100 | 100 | 90 | 100 | 100 | 100 | 0 | 97 | 100 |
|   | POS | 60 | 60 | 60 | 85 | 100 | 100 | 0 | 60 | 95 |
| 17 | PES | 0 | 0 | 0 | 0 | 0 | 0 | 0 | 0 | 0 |
|   | POS | 90 | 30 | 30 | 0 | 0 | 90 | 0 | 50 | 30 |
| 18 | PES | 100 | 0 | 0 | 0 | 100 | 100 | 0 | 33 | 67 |
|   | POS | 100 | 40 | 40 | 60 | 90 | 100 | 0 | 60 | 83 |
| 19 | PES | 100 | 75 | 70 | 0 | 0 | 100 | 0 | 82 | 33 |
|   | POS | 90 | 20 | 10 | 20 | 90 | 100 | 0 | 40 | 70 |
| 20 | PES | 0 | 0 | 0 | 0 | 0 | 0 | 0 | 0 | 0 |
|   | POS | 0 | 0 | 0 | 0 | 10 | 100 | 0 | 0 | 37 |
| 21 | PES | 100 | 0 | 0 | 0 | 10 | 60 | 0 | 33 | 23 |
|   | POS | 0 | 0 | 0 | 20 | 30 | 100 | 0 | 0 | 50 |
| 22 | PES | 90 | 0 | 10 | 100 | 0 | 0 | 0 | 33 | 33 |
|   | POS | 10 | 0 | 0 | 90 | 10 | 10 | 0 | 3 | 37 |
| 23 | PES | 100 | 0 | 0 | 0 | 0 | 0 | 0 | 33 | 0 |
|   | POS | 20 | 10 | 10 | 20 | 80 | 100 | 0 | 13 | 67 |
| 24 | PES | 100 | 20 | 20 | 0 | 0 | 80 | 0 | 47 | 27 |
|   | POS | 0 | 0 | 0 | 0 | 10 | 10 | 0 | 0 | 7 |
| 25 | PES | 100 | 10 | 10 | 0 | 100 | 100 | 0 | 40 | 67 |
|   | POS | 0 | 0 | 0 | 0 | 10 | 100 | 0 | 0 | 7 |
| 26 | PES | 0 | 0 | 0 | 80 | 20 | 20 | 0 | 0 | 40 |
|   | POS | 0 | 0 | 0 | 0 | 0 | 0 | 0 | 0 | 0 |
| 27 | PES | 100 | 0 | 0 | 0 | 0 | 0 | 0 | 33 | 0 |
|   | POS | 0 | 0 | 0 | 0 | 0 | 0 | 0 | 0 | 0 |
| 28 | PES | 100 | 50 | 80 | 100 | 100 | 100 | 0 | 77 | 100 |
|   | POS | 0 | 0 | 0 | 0 | 0 | 0 | 0 | 0 | 0 |
| 29 | PES | 80 | 10 | 20 | 80 | 20 | 20 | 0 | 37 | 40 |
|   | POS | 0 | 0 | 0 | 0 | 0 | 0 | 0 | 0 | 0 |
| 30 | PES | 0 | 0 | 100 | 100 | 100 | 100 | 0 | 33 | 100 |
|   | POS | 0 | 0 | 0 | 0 | 0 | 0 | 0 | 0 | 0 |
| 31 | PES | 100 | 90 | 100 | 100 | 100 | 100 | 0 | 97 | 100 |
|   | POS | 0 | 0 | 0 | 100 | 100 | 0 | 0 | 0 | 67 |
| 32 | PES | 0 | 0 | 0 | 0 | 0 | 0 | 0 | 0 | 0 |
|   | POS | 100 | 80 | 100 | 100 | 80 | 0 | 0 | 93 | 60 |
| 33 | PES | 100 | 100 | 100 | 100 | 100 | 100 | 0 | 100 | 100 |
|   | POS | 0 | 0 | 0 | 100 | 100 | 100 | 0 | 0 | 100 |
| 34 | PES | 100 | 100 | 100 | 100 | 100 | 60 | 0 | 100 | 87 |

TABLE 2-continued

| Compound No. | METHOD | SETVI | ECHCG AVEFA | PHBPU | ABUTH | SINAR | CYPES | AVG | AVB |
|---|---|---|---|---|---|---|---|---|---|
|  | POS | 0 | 0 | 0 | 0 | 0 | 0 | 0 | 0 | 0 |
| 35 | PES | 20 | 20 | 20 | 0 | 0 | 0 | 0 | 20 | 0 |
|  | POS | 0 | 0 | 0 | 100 | 100 | 100 | 0 | 0 | 100 |
| 36 | PES | 100 | 0 | 40 | 90 | 20 | 20 | 0 | 47 | 43 |
|  | POS | 20 | 0 | 0 | 100 | 85 | 40 | 0 | 7 | 75 |
| 37 | PES | 0 | 0 | 0 | 0 | 0 | 0 | 0 | 0 | 0 |
|  | POS | 10 | 40 | 30 | 75 | 80 | 10 | 0 | 27 | 55 |
| 38 | PES | 0 | 20 | 20 | 0 | 0 | 0 | 0 | 13 | 0 |
|  | POS | 0 | 0 | 0 | 100 | 100 | 0 | 0 | 0 | 67 |
| 39 | PES | 0 | 0 | 0 | 0 | 0 | 0 | 0 | 0 | 0 |
|  | POS | 0 | 0 | 0 | 80 | 80 | 0 | 0 | 0 | 53 |
| 40 | PES | 100 | 80 | 100 | 100 | 100 | 60 | 0 | 94 | 87 |
|  | POS | 100 | 100 | 100 | 100 | 100 | 80 | 0 | 100 | 93 |
| 41 | PES | 100 | 10 | 20 | 0 | 0 | 0 | 0 | 43 | 0 |
|  | POS | 0 | 0 | 0 | 0 | 0 | 0 | 0 | 0 | 0 |
| 42 | PES | 100 | 10 | 95 | 100 | 40 | 20 | 0 | 68 | 53 |
|  | POS | 90 | 50 | 20 | 100 | 50 | 40 | 0 | 53 | 63 |

FORMULATIONS

In practice, a pure compound can be used as a herbicide. However, in general, the compounds are first formulated with one or more inert carriers or diluents suitable for herbicidal use, before being applied.

The compositions or formulations, including a compound as described herein, may exist in any one of a number of solid or liquid forms. Examples of solid forms are dusts, granules, microcapsules, tablets, powders and the like. Examples of liquid forms are emulsifiable concentrates, flowables, liquid concentrates and pastes. Such compositions may contain, in addition to the active compound or compounds, various carriers or diluents; surface active agents (wetting agents, dispersing agents and/or emulsifying agents); solvents (water, or organic solvents such as aromatic solvents or chlorinated aliphatic solvents); adhesives; thickeners; binders; antifoaming agents; and other substances as mentioned herein. Solid carriers or diluents included in such compositions or formulations may include, for example, ground natural minerals such as kaolins, alumina, calcium carbonate, silica, clay, etc.; ground synthetic minerals such as various silicates and aluminosilicates and ground vegetable products such as bark, cornmeal, sawdust, cellulose powder and the like.

To manufacture solid compositions, the active substances are mixed with solid carriers or diluents such as those mentioned above and the mixture is ground to the appropriate size. Granules can be manufactured by dissolving an active compound in an organic solvent and applying the mixture, for example, by atomization, onto an absorptive granulated inert material, such as silica. Adhesives may be utilized to assist in the incorporation of the compound onto the solid particles.

Microcapsules consist of fully enclosed droplets or granules containing the active materials in which the enclosing material is an inert porous membrane, arranged to allow escape of the enclosed materials to the surrounding medium at controlled rates over a specified period of time. Encapsulated droplets are typically about 1 to 50 microns in diameter. The enclosed liquid typically constitutes about 50 to 95% of the weight of the entire capsule, and may contain an amount of solvent in addition to the active materials. Encapsulated granules are characterized by porous membranes sealing the openings of the granule carrier pores, trapping the liquid containing the active components inside for controlled release. A typical granule size ranges from 1 millimeter to 1 centimeter in diameter. In agricultural usage, the granule size is generally about 1 to 2 millimeters in diameter. Granules formed by extrusion, agglomeration or prilling are useful in the present invention, as well as the materials in their naturally occurring form. Examples of such carriers ar vermiculite, sintered clay granules, kaolin, attapulgite clay, sawdust and granular carbon. Useful encapsulating materials include natural and synthetic rubbers, cellulosic materials, styrene-butadiene copolymers, polyacrylo-nitriles, polyacrylates, polyesters, polyamides, polyureas, polyurethanes and starch xanthates.

Wettable powders, flowables, and pastes are obtained by mixing and milling an active compound with one or more dispersing/wetting agents and/or carriers or diluents. Common dispersing/wetting agents are, for example, lignins, methyl cellulose, naphthalenesulfonic acid derivatives, fatty alcohol sulfates and various types of alkali and alkaline earth metal salts of fatty acids.

Emulsifiable concentrates are generally obtained by dissolving the active compound in an organic solvent, for example, butanol, cyclohexanone, xylenes or higher boiling aromatic hydrocarbons. To obtain stable suspensions or emulsions in application water, wetting agents are generally also added.

It is possible to use highly concentrate liquid compositions containing up to about 95% by weight of the active compound, or even the active compound alone for those compounds which are liquids, when applying the compound in the form of a finely divided liquid by use of various atomizing equipment, for example by airplane crop spraying techniques. For other purposes, however, the various types of compositions which can be utilized for these compounds will contain varying amounts of the compound according to the type of composition and the intended use.

In general, compositions may contain from 0.1 to 95% of the active compound, more preferably from 0.5 to 90%. Some typical compositions will contain an active compound as follows: wettable powders, flowables and pastes—20 to 90% active compound; oil suspensions, emulsions, solutions and emulsifiable concentrates—1 to 90% active compound; aqueous suspensions—10 to 50% active compound; dusts and powders—1 to 25% active compound; granules and pellets—0.5 to 20% active compound.

The rate of application of the active compound to a locus to be controlled will depend on the nature of the seeds and plants to be controlled and will vary from about 0.05 to about 50 pounds per acre (about 0.06 to about 56 kg/ha).

In addition to the active compound and the various agents utilized in preparing compositions and formulations mentioned above, such compositions may also contain one or more other active compounds of the type mentioned herein as well as other pesticidal agents, such as herbicides, fungicides, insecticides, acaricides, nematocides, bactericides, and plant growth regulators. Such compositions may also contain soil disinfectants or fumigants and may further contain fertilizers, thus making it possible to provide multi-purpose compositions containing one or of the compounds described herein as well as, optionally, other pesticides and also fertilizers, all intended and formulated for use at the same locus.

Compositions containing one or more of the active compounds described, in a herbicidally effective amount, may be applied to the plant or locus to be controlled in any conventional manner. Thus, powders and various liquid compositions containing the active compound can be applied by the use of power dusters, boom and hand sprayers and spray dusters, or applied from airplanes as mists or sprays. When applied in the latter method they may be effective in very low dosages. To modify or control growth of germinating seeds or emerging seedlings liquid compositions may be applied to the soil with conventional methods and may be distributed in the soil to a depth of one-half inch below the soil surface. The compositions need not be admixed with the soil particles but can be applied merely by sprinkling on the surface of the soil.

Compositions including active compounds may also be applied by addition to irrigation waters supplied to the field to be treated. This method of application permits penetration of the compounds into the soil as the water is absorbed therein.

| EXAMPLES OF TYPICAL COMPOSITIONS | | | |
|---|---|---|---|
| Oil | | | |
| Ingredient | Weight % | | |
| Compound 1 | 1 | | |
| Oil solvent-heavy aromatic naphtha | 99 | | |
| Total | 100 | | |
| Emulsifiable Concentrate | | | |
| Compound 2 | 50 | | |
| Kerosene | 45 | | |
| Emulsifying agent (mixture of long chain ethoxylated polyethers with long chain sulfonate) | 5 | | |
| Total | 100 | | |
| Emulsifiable Concentrate | | | |
| Compound 3 | 90 | | |
| Kerosene | 5 | | |
| Emulsifying agent (mixture of long chain ethoxylated polyethers with long chain sulfonate) | 5 | | |
| Total | 100 | | |
| Dusts and/or Powders | | | |
| Ingredient | Wt. % | Wt. % | Wt. % |
| Compound 4 | 0.5 | 50.0 | 90.0 |
| Attapulgite Clay Powder | 93.5 | 44.0 | 4.0 |
| Sodium lignin sulfonate | 5.0 | 5.0 | 5.0 |

| -continued | | | |
|---|---|---|---|
| EXAMPLES OF TYPICAL COMPOSITIONS | | | |
| Sodium dioctyl sulfosuccinate | 1.0 | 1.0 | 1.0 |
| Total | 100.0 | 100.0 | 100.0 |

What is claimed is:

1. A compound having the formula

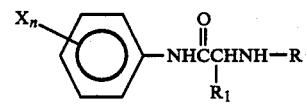

wherein R is $C_1$-$C_3$ lower alkyl; $R_1$ is phenyl substituted with phenoxy, benzyloxy, nitro or one or more $C_1$-$C_3$ lower alkyl, $C_1$-$C_3$ lower alkoxy, halo, haloalkyl or combinations thereof; X is halo, haloalkyl or combinations thereof; and n is an integer from 0-3, inclusive.

2. A compound according to claim 1 wherein $R_1$ is phenyl substituted with phenoxy or benzyloxy, X is fluoro and n is the integer 2.

3. A compound according to claim 1 wherein $R_1$ is phenyl substituted with lower alkoxy, X is fluoro and n is the integer 2.

4. A compound according to claim 1 wherein $R_1$ is phenyl substituted with $C_1$-$C_3$ lower alkyl, X is fluoro and n is the integer 2.

5. A compound according to claim 1 wherein $R_1$ is phenyl substituted with nitro, X is haloalkyl and n is the integer 1.

6. An herbicidal composition comprising:
(a) an herbicidally effective amount of a compound having the formula wherein R is $C_1$-$C_3$ lower alkyl; $R_1$ is phenyl substituted with phenoxy, benzyloxy, nitro or one or more $C_1$-$C_3$ lower alkyl, $C_1$-$C_3$ lower alkoxy, halo, haloalkyl or combinations thereof; X is halo, haloalkyl or combinations thereof; and n is an integer from 0-3, inclusive; and
(b) an inert diluent carrier therefor.

7. An herbicidal composition according to claim 6 wherein $R_1$ is phenyl substituted with alkyl, X is halo and n is the integer 2.

8. An herbicidal composition according to claim 6 wherein $R_1$ is phenyl substituted with phenoxy or benzyloxy, X is fluoro and n is the integer 2.

9. An herbicidal composition according to claim 8 wherein X is chloro or fluoro and n is an integer from 1-2, inclusive.

10. An herbicidal composition according to claim 6 wherein X is chloro and n is an integer from 1-2, inclusive.

11. An herbicidal composition according to claim 6 wherein X is fluoro and n is an integer from 1-2, inclusive.

12. An herbicidal composition according to claim 6 wherein X is haloalkyl and n is the integer 1.

13. An herbicidal composition according to claim 6 wherein $R_1$ is phenyl substituted with lower alkoxy, X is fluoro and n is the integer 2.

14. An herbicidal composition according to claim 6 wherein $R_1$ is phenyl substituted with $C_1$-$C_3$ lower alkyl, X is fluoro and n is the integer 2.

15. An herbicidal composition according to claim 6 wherein $R_1$ is phenyl substituted with nitro, X is haloalky and n is the integer 1.

16. A method of controlling undesirable vegetation comprising applying to said vegetation or the locus thereof, an herbicidally effective amount of a compound having the formula

wherein
R is $C_1$–$C_3$ lower alkyl;
$R_1$ is hydrogen, $C_1$–$C_3$ lower alkyl, phenyl, phenyl substituted with phenoxy, benzyloxy, nitro or phenyl substituted with alkyl, alkoxy, haloalkyl, one or more halo or combinations thereof;
X is alkyl, halo, haloalkyl or combinations thereof; and
n is an integer from 0–3, inclusive.

17. A method according to claim 16 wherein $R_1$ is hydrogen, $C_1$–$C_3$ lower alkyl, phenyl, phenyl substituted with phenoxy, benzyloxy or one or more $C_1$–$C_3$ alkyl, $C_1$–$C_3$ alkoxy, halo, haloalkyl combinations or thereof; X is $C_1$–$C_3$ lower alkyl, halo or haloalkyl and n is an integer from 0–3, inclusive.

18. A method according to claim 17 wherein $R_1$ is hydrogen, X is halo or haloalkyl and n is an integer from 1–2, inclusive.

19. A method according to claim 18 wherein X is halo.

20. A method according to claim 18 wherein X is haloalkyl and n is the integer 1.

21. A method according to claim 17 wherein $R_1$ i $C_1$–$C_3$ alkyl, X is fluoro and n is the integer 3.

22. A method according claim 17 wherein $R_1$ is phenyl substituted with alkyl, X is halo and n is the integer 2.

23. A method according to claim 17 wherein $R_1$ is phenyl, phenyl substituted with phenoxy, benzyloxy or one or more $C_1$–$C_3$ lower alkyl, $C_1$–$C_3$ lower alkoxy, halo, haloalkyl or combinations; X is halo, haloalkyl or combinations thereof; and n is an integer from 0–3, inclusive.

24. A method according to claim 23 wherein $R_1$ is phenyl substituted with phenoxy or benzyloxy, X is fluoro and n is the integer 2.

25. A method according to claim 23 wherein $R_1$ is phenyl, X is halo, haloalkyl or combinations thereof and n is an integer from 1–2, inclusive.

26. A method according to claim 24 wherein X is chloro or fluoro, and n is an integer from 1–2, inclusive.

27. A method according to claim 25 wherein X is chloro and n is an integer from 1–2, inclusive.

28. A method according to claim 26 wherein X is fluoro and n is an integer from 1–2, inclusive.

29. A method according to claim 26 wherein X is haloalkyl and n is the integer 1.

30. A method according to claim 25 wherein $R_1$ is phenyl substituted with lower alkoxy, X is fluoro and n is the integer 2.

31. A method according to claim 25 wherein $R_1$ is phenyl substituted with $C_1$–$C_3$ lower alkyl, X is fluoro and n is the integer 2.

32. A method according to claim 25 wherein $R_1$ is phenyl substituted with nitro, X is haloalkyl and n is the integer 1.

* * * * *